(12) United States Patent
Rasmussen et al.

(10) Patent No.: US 10,561,757 B2
(45) Date of Patent: Feb. 18, 2020

(54) SCENT DIFFUSER WITH INTERACTIVE BODY PORTION

(71) Applicant: Energizer Brands II, LLC, St. Louis, MO (US)

(72) Inventors: Kathy Rasmussen, St. Louis, MO (US); Raul Garcia, St. Louis, MO (US)

(73) Assignee: Energizer Brands II, LLC, St. Louis, MO (US)

( * ) Notice: Subject to any disclaimer, the term of this patent is extended or adjusted under 35 U.S.C. 154(b) by 173 days.

(21) Appl. No.: 15/583,604

(22) Filed: May 1, 2017

(65) Prior Publication Data

US 2018/0311393 A1    Nov. 1, 2018

(51) Int. Cl.
*A61L 9/12* (2006.01)
*B60H 3/00* (2006.01)

(52) U.S. Cl.
CPC .............. *A61L 9/12* (2013.01); *B60H 3/0007* (2013.01); *A61L 2209/15* (2013.01)

(58) Field of Classification Search
CPC . A61L 9/12; A61L 9/125; A61L 9/127; A61L 2209/10; A61L 2209/13; A61L 2209/133; A61L 2209/15; B60H 3/0007–0035; B60H 2003/0042–0064
USPC ....................... 239/34, 53–60; D23/366–369
See application file for complete search history.

(56) References Cited

U.S. PATENT DOCUMENTS

| | | | | |
|---|---|---|---|---|
| 4,523,717 | A * | 6/1985 | Schwab .............. | A01M 31/008 206/225 |
| 5,865,372 | A * | 2/1999 | Ceresko .................... | A61L 9/03 239/60 |
| 5,947,379 | A * | 9/1999 | Freeman ............. | A01M 31/008 239/52 |
| 6,764,656 | B1 * | 7/2004 | Matulevich ............... | A61L 9/12 422/124 |
| 7,246,732 | B1 * | 7/2007 | Ha ......................... | A63H 17/00 224/282 |
| D674,071 | S * | 1/2013 | Browder ...................... | D23/367 |
| 2006/0071092 | A1 * | 4/2006 | Harris, Jr. ........... | A01M 1/2044 239/44 |

(Continued)

OTHER PUBLICATIONS

Home Depot, "3/8-inch Zinc-Plated Spring Snap Hook", Mar. 7, 2016, <https://www.homedepot.com/p/Everbilt-3-8-in-Zinc-Plated-Spring-Snap-Hook-44134/205874119> (Year: 2016).*

*Primary Examiner* — Cody J Lieuwen
(74) *Attorney, Agent, or Firm* — Armstrong Teasdale

(57) ABSTRACT

A scent diffuser (e.g., an air freshener) may be configured to resemble a desired shape, such as the shape of an animal. The scent diffuser may comprise an interactive body portion, a fragrance emitter, and a support component configured to support the body portion and the fragrance emitter. The interactive body portion comprises a base; a cover secured relative to the base; and a pivot member movably secured relative to the cover, wherein the pivot member is configured to pivot, bob, or otherwise move freely relative to the cover upon application of an external force to the pivot member. The fragrance emitter is secured relative to the base of the interactive body portion, and the fragrance emitter comprises a fragrance composition configured to diffuse into an environment surrounding the scent diffuser.

14 Claims, 4 Drawing Sheets

(56) References Cited

U.S. PATENT DOCUMENTS

| | | | | |
|---|---|---|---|---|
| 2007/0119963 A1* | 5/2007 | DiBello | ............... | A61L 9/127 239/34 |
| 2014/0113538 A1* | 4/2014 | Irvin | ............... | A61L 9/12 454/156 |
| 2014/0145004 A1* | 5/2014 | Westphal | ............... | A61L 9/12 239/59 |
| 2014/0367484 A1* | 12/2014 | Kramer | ............... | A61L 9/12 239/44 |

* cited by examiner

SCENT DIFFUSER WITH INTERACTIVE BODY PORTION

BACKGROUND

Consumer taste for features included in scent diffusers (e.g., air fresheners) are constantly changing. Accordingly, a need constantly exists for scent diffuser configurations designed to match consumers continually evolving tastes.

BRIEF SUMMARY

Various embodiments are directed to scent diffusers having an interactive body portion having at least one mechanically movable feature configured for movement when subject to an external force. The body portion may take any of a variety of forms, such as a three-dimensional representation of an animal, and may include at least one feature (e.g., visually representative of a head and neck of the animal) that is pivotably secured to other portions of the body portion and is configured to pivot freely relative to the body portion.

The body portion itself at least partially houses a solid fragrance mass configured to emit a desired scent from the scent diffuser, for example through sublimation of the fragrance mass itself and/or though evaporation of a fragrance liquid (e.g., oil) saturating the fragrance mass. The body portion and the solid fragrance may are supported by a support component, such as a support stand configured to support the combination of the body portion and the solid fragrance mass off of a support surface, such as the dashboard of an automobile interior.

Various embodiments are directed to a scent diffuser (e.g., an air freshener) having an interactive body portion. In various embodiments, the scent diffuser comprises an interactive body portion (e.g., resembling a turtle) comprising: a base; a cover secured relative to the base; and a pivot member movably secured relative to the cover, wherein the pivot member is configured to pivot freely relative to the cover upon application of an external force to the pivot member; a fragrance emitter comprising a fragrance composition configured to diffuse into an environment surrounding the scent diffuser, wherein the fragrance emitter is secured relative to the base of the interactive body portion; and a support component defining a support base and a support rod, wherein the support rod engages the fragrance emitter to support the fragrance emitter and the interactive body portion above the support component, and the support base is configured to rest on a support surface to support the scent diffuser above the support surface.

In certain embodiments, the cover comprises a hollow cover body defining a cover aperture extending through a sidewall of the cover body, and the pivot member is suspended by a support line positioned within the hollow cover body such that a portion of the pivot member extends through the aperture. Moreover, in various embodiments, the base defines an at least substantially planar top surface, and the bottom surface defines a lower cavity therein. In such embodiments, the fragrance emitter may be configured to nest within the lower cavity when secured relative to the base.

BRIEF DESCRIPTION OF THE SEVERAL VIEWS OF THE DRAWINGS

Reference will now be made to the accompanying drawings, which are not necessarily drawn to scale, and wherein.

DETAILED DESCRIPTION

The present disclosure more fully describes various embodiments of a scent diffuser (e.g., an air freshener) with reference to the accompanying drawings. It should be understood that some, but not all embodiments are shown and described herein. Indeed, the embodiments may take many different forms, and accordingly this disclosure should not be construed as limited to the embodiments set forth herein. Rather, these embodiments are provided so that this disclosure will satisfy applicable legal requirements. Like numbers refer to like elements throughout.

Various embodiments are directed to scent diffusers (e.g., air fresheners) configured for diffusing a fragrance (e.g., a scented oil or other material having a desirable odor) into environmental air surrounding the scent diffuser. Specifically, various embodiments are specifically configured for use in an automobile interior.

Various embodiments are directed to scent diffusers having an interactive body portion having one or more movable features that provides aesthetically pleasing movement when subject to an external force. For example, the body portion may be configured to resemble an animal having one or more movable appendages configured to move (e.g., oscillate, bob, and/or the like) in response to an external force. The scent diffuser itself may be configured for placement within an automobile interior, and thus the movable portions of the body portion of various embodiments may be configured to oscillate as the vehicle—and accordingly the scent diffuser—is jostled during vehicle travel.

In various embodiments, the body portion of the scent diffuser at least partially houses or otherwise covers a solid fragrance emitter (e.g., a fragrance mass or a solid body saturated with a fragrance liquid). For example, the body portion may define a cavity having an open bottom end, and the solid fragrance emitter may be at least partially nested within the open bottom end. In certain embodiments, the fragrance emitter may be configured to resemble part of an animal, such that collectively, the body portion and fragrance emitter resemble an animal. As just one non-limiting example, the body portion and the fragrance emitter may collectively resemble a turtle, with the fragrance emitter specifically resembling the stomach of the turtle. In certain embodiments, the head and neck may be movably secured relative to the body portion, such that the head and neck oscillate when subject to an external force.

The body portion and fragrance emitter may be supported by a support component, such as a base configured to support the body portion and fragrance emitter above a support surface.

Figure 1:
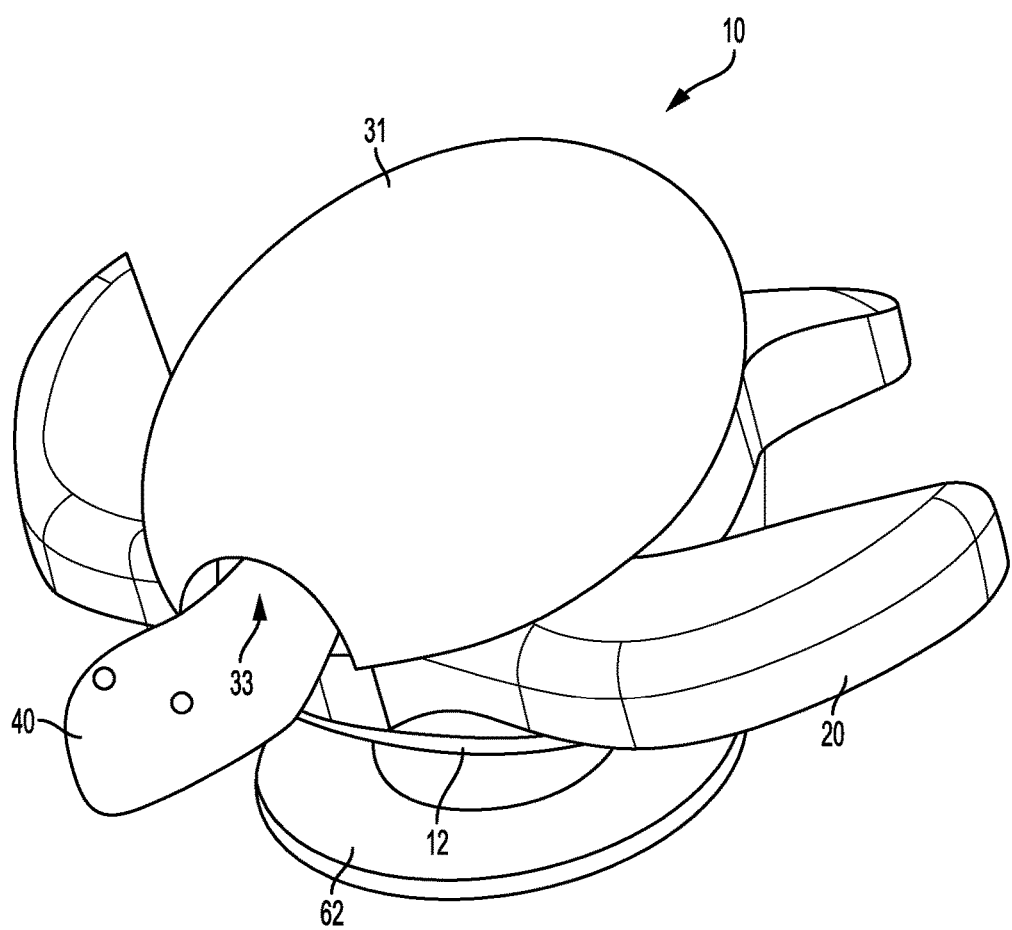
FIG. 1 shows a scent diffuser according to one embodiment.
Figure 2:
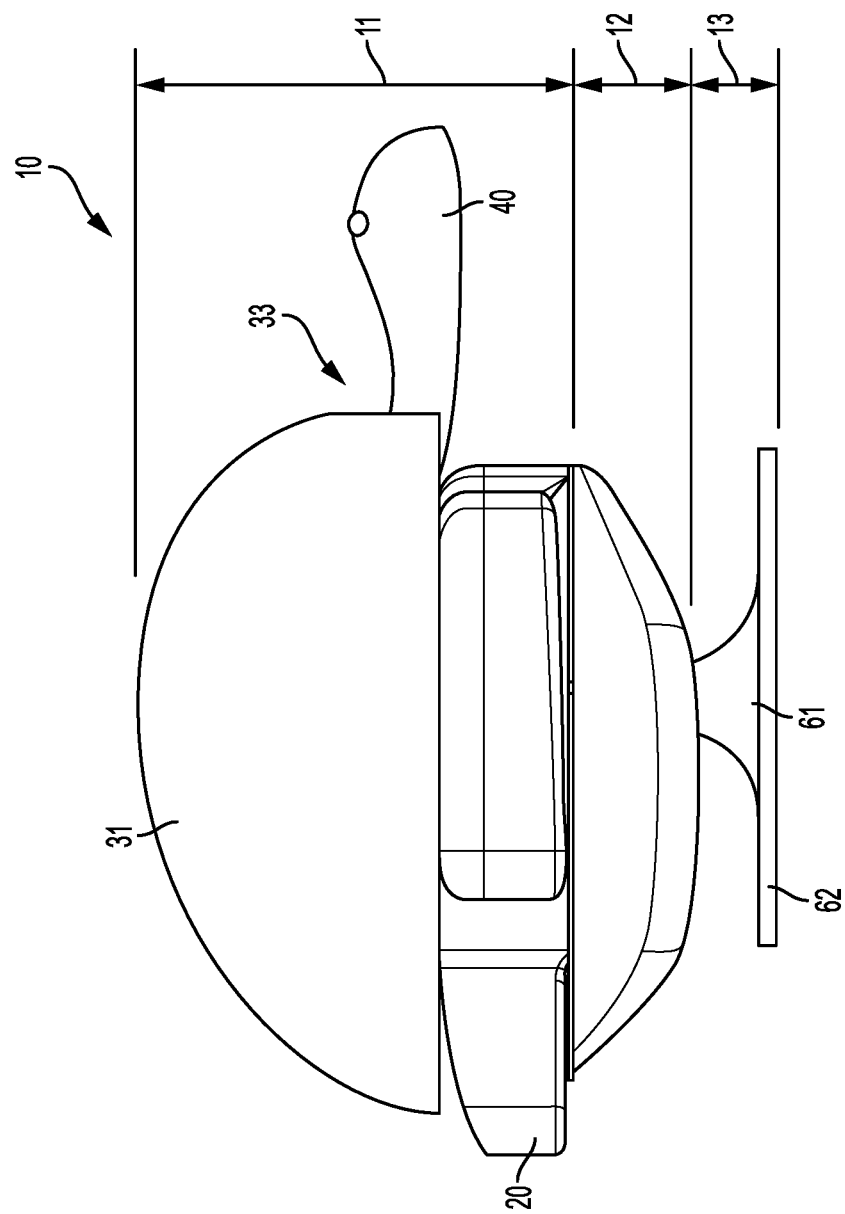
FIG. 2 shows a side view of the scent diffuser of FIG. 1.
Figure 3:
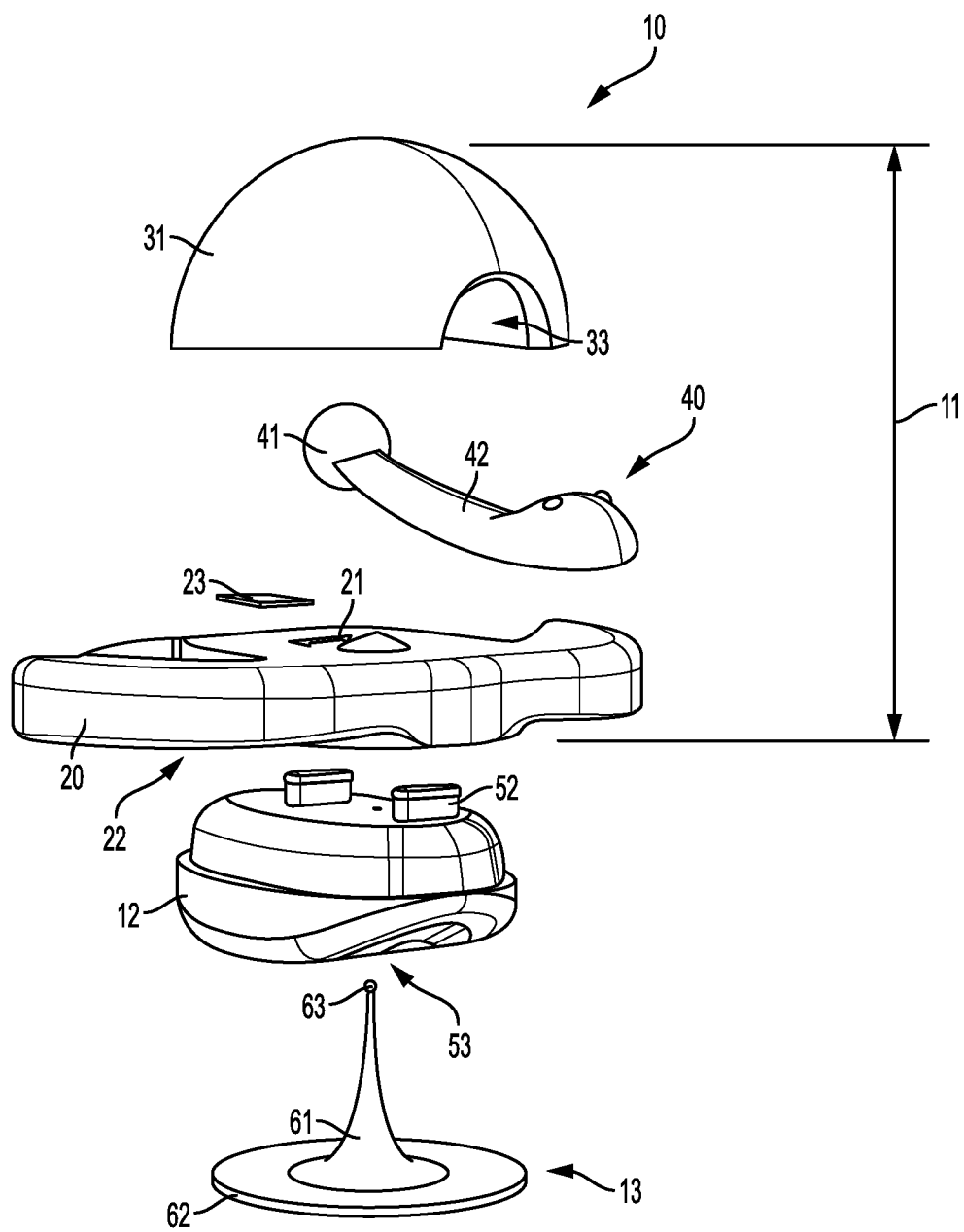
FIG. 3 shows an exploded view of the scent diffuser of FIG. 1.

In particular, FIGS. 1-3 provide various views of a scent diffuser 10 according to one embodiment. As shown in the figures, the scent diffuser 10 comprises a body portion 11, a fragrance emitter 12, and a support component 13. As will be discussed in greater detail herein, body portion 11 and fragrance emitter 12 collectively resemble a turtle having a shell and appendages formed by portions of the body portion 11 and a stomach formed by at least a portion of the fragrance emitter 12. However, it should be understood that the scent diffuser 10 may have any of a variety of configurations, and accordingly may resemble any of a variety of items, objects, animals, persons, and/or the like.

With reference again to the forgoing figures, the body portion 11 may comprise a cover body 31 (e.g., resembling a turtle shell), a base 20 (e.g., resembling various extremities of a turtle), and a pivot member 40 (e.g., resembling a turtle head and neck). Each of the body portion 11 components may comprise any of a variety of rigid materials, such as wood, metal, plastic (PVC, HDPE, various polymers, and/or the like), and/or the like. As just one example, the cover body 31 may comprise wood and each of the base 20 and pivot member 40 may comprise a metal material.

Figure 4:
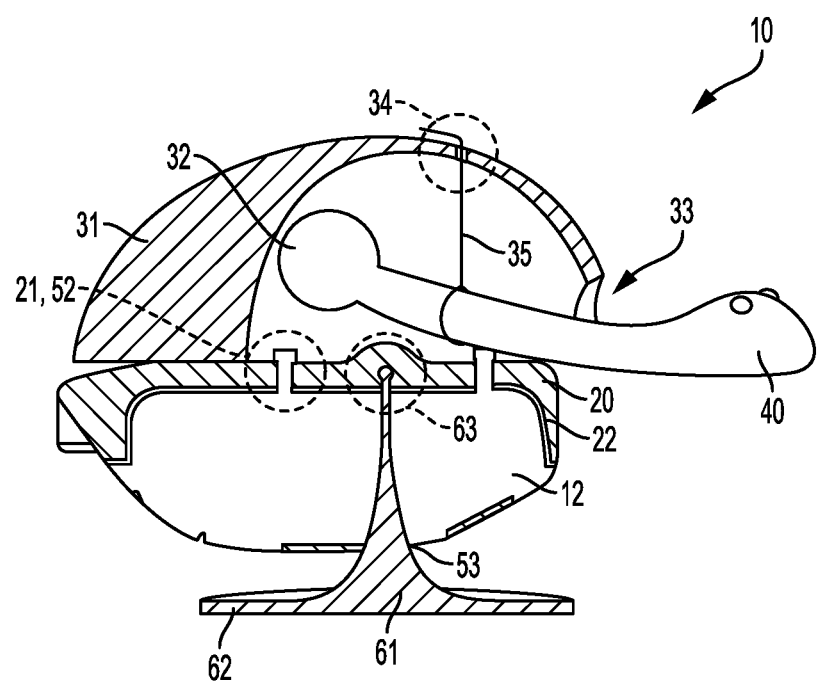
FIG. 4 shows a side cutaway view of the scent diffuser of FIG. 1.

As illustrated in the figures, the pivot member 40 may comprise a base component 41, such as the ball shown in FIG. 3, and a lever arm 42 extending away from one side of the base component 41. With reference briefly to the cutaway view of FIG. 4, the base component 41 may operate as a counterweight to balance the pivot member 40 within the cover body 31. As shown in FIG. 4, the cover body 31 may be hollow, and the pivot member 40 may be suspended partially within the cover body 31 by a flexible support line 35 (e.g., a string) extending from a hole 34 within a top surface of the cover body 31. The support line 35 may be secured to the pivot member 40 at a support line engagement point located proximate a central portion of the pivot member 40, such that the weight of the pivot member 40 is at least substantially balanced on each side of the support line 35. Moreover, as shown in the figures, a portion of the pivot member 40 (e.g., resembling a head and neck of a turtle) extends through the cover body 31 through the cover aperture 33 such that it is visible outside of the cover body 31. In the illustrated embodiment, the cover aperture 33 is larger than a cross-section of the lever arm 42, such that the lever arm 42 can oscillate, bob, and/or otherwise move freely relative to the cover aperture 33. Thus, upon application of an external force, such as due to moving the scent diffuser 10 and/or the pivot member 40, the pivot member 40 oscillates freely within scent diffuser 10.

As another example embodiment, the base component 41 may be pivotably secured within a rotation socket (e.g., a ball-joint) of the cover portion 31, such that the pivot member 40 is freely pivotable about the base component 41. The lever arm 42 extends away from the base component 41 and the rotation socket through the cover aperture 33 extending through a side portion of the cover body 31.

In certain embodiments, the pivot member 40 may be configured for three-dimensions of movement. Accordingly, the lever arm 42 may be enabled to pivot up-and-down; left-and-right; and to twist about an axis extending along the length of the pivot member 40 relative to the remaining portions of the scent diffuser 10. In certain embodiments, the lever arm 42 may translate into-and-out of the cover body 31 and/or left-and-right relative to the cover body 31 (e.g., pivoting about a pivot point formed where the support line 35 intersects the hole 34). As yet another example, the lever arm 42 may move up-and-down relative to the cover body 31 (e.g., by creating slack within the support line 35). The lever arm 42 may be freely movable between movement limits established based on the intersection of the lever arm 42 with various other portions of the body portion 11 (e.g., the cover body 31 and/or the base 20). For example, the lever arm 42 may pivot/move upward until a portion of the lever arm 42 contacts a portion of the cover body 31 (e.g., proximate cover aperture 22); the lever arm 42 may pivot/move downward until a portion of the lever arm 42 contacts a portion of the base 20; and the lever arm 42 may pivot/move side-to-side until a portion of the lever arm 42 contacts a portion of the cover body 31.

In certain embodiments, the interface between the base component 41 and the rotation socket may be a low-friction interface, such that slight movements of either the pivot member 40 or the body portion 11 (e.g., movements caused by a vehicle in which the scent diffuser 10 is mounted) cause the pivot member 40 to pivot relative to the body portion 11.

Moreover, the base component 41 may be eccentrically weighted to bias a majority of the weight of the base component 41 to a bottom portion of the base component 41 (e.g., a component proximate the base 20 when mounted in the rotation socket. Biasing the weight of the base component 41 toward the bottom portion of the base component 41 may cause the lever arm 42 to be positioned between the body 20 and the cover body 31 such that the lever arm 42 is not in contact with either the base 20 or the cover body 31 when in a neutral, steady-state position (e.g., when no force is applied to the pivot member 40 or the body portion 11). Accordingly, upon the application of an external force, the pivot member 40 may oscillate relative to the body portion 31 until eventually settling in the neutral position. However, it should be understood that the base component 41 (and/or the entirety of the pivot member 40) may be at least substantially equally weighted) to facilitate a desired movement type. For example, embodiments in which the pivot member 40 is suspended by a support line 35 may comprise a pivot member 40 having at least equally distributed weight.

It should be understood that the base component 41 and rotation socket may be embodied as any of a variety of pivot joints, such as a hinge, a two-dimension of freedom ball joint, and/or the like. Moreover, the base component 41 may have the weight thereof biased in a variety of configurations, such that the lever arm 42 is supported by the base 20 when in the neutral position, such that the lever arm 42 rests against a portion of the cover body 31 when in the neutral position, and/or the like.

Moreover, in the illustrated embodiment, the cover body 31 is secured relative to the base 20 via an adhesive material 23 (e.g., an adhesive tape, an adhesive composition, and/or the like). Although not shown, the cover body 31 may define one or more alignment features (e.g., pins, slots, tabs, and/or the like) configured to interact with corresponding alignment features of the base 20. In certain embodiments, the alignment features may be configured to secure the cover body 31 relative to the base 20. For example, the one or more alignment features may comprise locking tabs and corresponding slots, locking pins, and/or the like. However, in certain embodiments, the cover body 31 may be secured relative to the base 20 via one or more fasteners (e.g., screws, nails, and/or the like).

As shown in the figures, the base 20 may comprise a central portion located generally within the perimeter of the cover body 31, and one or more appendages extending beyond the perimeter of the cover body 31. Accordingly, the base 20 may have any of a variety of forms, to give the body portion 11 any of a variety of aesthetics.

Moreover, the base 20 may define one or more coupling features configured to secure the base 20 relative to the fragrance emitter 12. For example, base 20 shown in the illustrated embodiment defines a plurality of coupling slots 21 configured to accept corresponding coupling tabs 52 of the fragrance emitter 12. The base 20 of the illustrated embodiment further defines a lower cavity 22 having an open bottom end extending into a bottom surface of the base 20. The described coupling slots 21 extend between a top surface of the base 20 and an inner surface of the lower cavity 22. The lower cavity 22 may have a cross-sectional size and orientation and a depth configured to accept an upper portion of the fragrance emitter 12. For example, in the illustrated embodiments, the upper portion of the fragrance emitter 12 defines the plurality of coupling tabs 52 extending at least substantially vertically away from a top surface of the fragrance emitter 12. Moreover, sidewalls and a top surface of the fragrance emitter 12 may have a size and shape corresponding to the configuration of the lower cavity 22 of the base 20, such that the upper portion of the fragrance emitter 12 is configured to nest within the lower cavity 22. In the illustrated embodiment of FIG. 3, the fragrance emitter 12 defines an at least substantially horizontal ledge separating the upper portion and lower portion of the fragrance emitter 12, the ledge extending outward between the sidewalls of the upper portion of the fragrance emitter 12 to the sidewalls of the lower portion of the fragrance emitter 12. In such embodiments, the cross-section of the upper portion of the fragrance emitter 12 (e.g., parallel to the surface of the ledge) has a smaller area than a parallel cross-section of the lower portion of the fragrance emitter 12. The ledge may have a width (e.g., measured as the distance between the sidewalls of the upper portion and the lower portion of the fragrance emitter 12) at least equal to the distance between the sidewalls of the upper portion of the fragrance emitter 12 and parallel interior sidewalls of the lower cavity 22 of the base 20 (measured in a direction parallel with the surface of the ledge) when the fragrance emitter 12 is secured within the lower cavity 22. Accordingly, the lower portion of the fragrance emitter 12 has a cross-section larger than the interior cross-section of the lower cavity 22, and accordingly the ledge (and the lower portion of the fragrance emitter 12) covers any gap existing between the upper portion of the fragrance emitter 12 and the lower cavity 22. Said another way, the lower cavity 22 is not visible when the fragrance emitter 12 is secured within the lower cavity 22.

Moreover, as shown in the figures, the lower portion of the fragrance emitter 12 may be configured to resemble a portion of an animal or any of a variety of desired shapes. Thus, the lower surface of the fragrance emitter 12 may have one or more curves, grooves, protrusions, and/or the like that have a desired shape.

The fragrance emitter 12 may comprise any of a variety of scented materials. As non-limiting examples, the fragrance emitter 12 may comprise a plastic material (e.g., a polymer) saturated with a fragrance composition (e.g., a fragrance oil), and the fragrance composition may be configured to migrate to the surface of the plastic material over time, and to evaporate into the environment surrounding the scent diffuser 10. As yet another example, the fragrance emitter 12 may comprise a solid fragrance composition configured to sublimate over time into the environment surrounding the scent diffuser 10. As yet another example, the fragrance emitter 12 may comprise a wood material saturated with a fragrance composition configured to migrate to the surface of the fragrance emitter 12 and to evaporate into the environment surrounding the scent diffuser. As yet another example, the fragrance emitter 12, may comprise an impermeable rigid mesh material supporting a fragrance gel composition configured to evaporate and dissipate into the environment surrounding the scent diffuser 12. Accordingly, the fragrance emitter 12 may have any of a variety of configurations for emitting a fragrance into an environment surrounding the scent diffuser 10.

In the illustrated embodiment, the body portion 11 and fragrance emitter 12 are collectively supported by the support component 13. The support component 13 is positioned below the body portion 11 and fragrance emitter 12, such that the support component 13 supports the weight of the body portion 11 and fragrance emitter 12 above a support surface on which the scent diffuser 10 is positioned. For example, the support component 13 may be configured to support the scent diffuser 10 on a dashboard of an automobile interior.

As shown in FIG. 3, the support component 13 comprises a support base 62 defining a bottom surface against which the support component 13 rests on a support surface. The support component 13 additionally comprises a support rod 61 extending away from a top surface of the support base 62 and terminating at an engagement feature 63 located away from the support base 62, and configured to engage at least a portion of the fragrance emitter 12 and/or body portion 11 to secure the support component 13 relative to the body portion 11 and fragrance emitter 12. As shown in the figures, the support rod 61 is configured to engage a corresponding support aperture 53 defined in a bottom surface of the fragrance emitter 12. The support aperture 53 extends at least partially along the height of the fragrance emitter 12 (e.g., measured between the bottom surface and the top surface of the fragrance emitter 12) to provide a secure connection between the support rod 61 and the fragrance emitter 12. As shown in the cutaway view of FIG. 4, the support aperture 53 extends entirely through the fragrance emitter 12, such that the engagement feature 63 extends into a corresponding aperture within the base 20. In the illustrated embodiment, the engagement feature 63 has an enlarged diameter relative to an adjacent portion of the support rod 62, and accordingly the engagement feature 63 may be configured to snap into the corresponding aperture of the base 20 to form an interference fit therebetween, such that the support component 13 is securely attached relative to the base 20 and the fragrance emitter 12.

Moreover, as shown in FIG. 3, the support rod 61 may have an at least substantially conical shape (e.g., a curved cone), and the support aperture 53 may have a corresponding conical (e.g., curved cone) interior surface configured to accept the support rod 61 therein. Specifically, the support rod 61 may have a first diameter proximate the support base 61, and a second diameter proximate an opposite, upper end of the support rod 61, wherein the second diameter is smaller than the first diameter. The support aperture 53 may similarly have a third diameter proximate the bottom surface of the fragrance emitter 12, and a fourth diameter at an opposite, upper end of the support aperture 53, wherein the third diameter is substantially the same as the first diameter, and the fourth diameter is substantially the same as the second diameter. Accordingly, the support rod 61 may be configured to nest within the support aperture 53 as shown in FIG. 2 to support the fragrance emitter 12 and the body portion 11 on the support component 13 such that the fragrance emitter 12 and body portion 11 are immovable relative to the support component 13.

The support component 13 may comprise any of a variety of rigid and/or flexible components that may support the weight of the fragrance emitter 12 and the body portion 11 thereon. For example, the support component 13 may comprise a rigid plastic material (e.g., PVC) a wood material, a metal material, and/or the like. In certain embodiments, the support component 13 may comprise a plurality of materials. For example, the support rod 61 may comprise a rigid material, and the support base 62 may comprise a flexible material, such as a suction cup configured to detachably secure the scent diffuser 10 relative to a support surface. As an additional example, the support base 62 may comprise a rigid material, and an adhesive layer may be secured relative to the bottom surface of the support base 62 to secure the support base relative to a support surface.

CONCLUSION

Many modifications and other embodiments will come to mind to one skilled in the art to which this disclosure pertains having the benefit of the teachings presented in the foregoing descriptions and the associated drawings. Therefore, it is to be understood that the disclosure is not to be limited to the specific embodiments disclosed and that modifications and other embodiments are intended to be included within the scope of the appended claims. Although specific terms are employed herein, they are used in a generic and descriptive sense only and not for purposes of limitation.

That which is claimed:

1. A scent diffuser, the scent diffuser comprising:
an interactive body portion comprising:
a base;
a cover secured relative to the base, wherein the cover defines a hollow cover body defining a cover aperture extending through a sidewall of the cover body; and
a pivot member suspended within the hollow cover body by a flexible support line such that a portion of the pivot member extends through the cover aperture, wherein the pivot member is configured to pivot freely relative to the cover upon application of an external force to the pivot member;
a fragrance emitter comprising a fragrance composition configured to diffuse into an environment surrounding the scent diffuser, wherein the fragrance emitter is secured relative to the base of the interactive body portion; and
a support component defining a support base and a support rod, wherein the support rod engages the fragrance emitter to support the fragrance emitter and the interactive body portion above the support component, and the support base is configured to rest on a support surface to support the scent diffuser above the support surface.

2. The scent diffuser of claim 1, wherein the flexible support line engages the pivot member at a support line engagement point along a length of the pivot member where the weight of the pivot member is at least substantially balanced on either side of the support line engagement point.

3. The scent diffuser of claim 1, wherein the base defines an at least substantially planar top surface and an opposite bottom surface defining a lower cavity extending therein; and
wherein the fragrance emitter is secured within the lower cavity of the base.

4. The scent diffuser of claim 3, wherein the base defines one or more coupling apertures extending between the top surface of the base and an interior surface of the lower cavity; and
the fragrance emitter defines one or more coupling protrusions extending away from a top surface of the fragrance emitter, wherein the one or more coupling protrusions are configured to engage corresponding coupling apertures of the base to secure the fragrance emitter relative to the base.

5. The scent diffuser of claim 3, wherein the fragrance emitter defines:
an upper portion having a horizontal cross-section corresponding to a horizontal cross-section of the lower cavity; and
a lower portion having a horizontal cross-section larger than the horizontal cross-section of the lower cavity, such that the lower portion of the fragrance emitter covers at least a portion of an opening of the lower cavity of the base.

6. The scent diffuser of claim 1, wherein the fragrance emitter defines a support aperture extending at least partially between a bottom surface and a top surface of the fragrance emitter, and
wherein the support rod of the support base extends into the support aperture of the fragrance emitter to support the fragrance emitter and the interactive body portion.

7. The scent diffuser of claim 6, wherein the support aperture extends through the fragrance emitter between the bottom surface and the top surface, and
wherein the support rod of the support base extends through the support aperture and engages a portion of the base to support the fragrance emitter and the interactive body portion.

8. The scent diffuser of claim 6, wherein the support rod has a curved conical sidewall and the support aperture has a corresponding curved conical interior such that the sidewall of the support rod engages the corresponding curved conical interior of the support aperture.

9. The scent diffuser of claim 1, wherein the support base comprises a fastener to secure the scent diffuser relative to the support surface.

10. The scent diffuser of claim 1, wherein the cover is secured relative to the base with an adhesive material.

11. The scent diffuser of claim 1, wherein the interactive body portion resembles a turtle.

12. The scent diffuser of claim 1, wherein the fragrance emitter comprises a polymer composition in which the fragrance composition migrates to the surface of the polymer composition over time.

13. The scent diffuser of claim 1, wherein the cover comprises a wood material and at least one of the base and the pivot member comprises a metal material.

14. The scent diffuser of claim 1, wherein the support component is rigidly secured relative to the fragrance emitter to impede movement of the fragrance emitter relative to the support component.

* * * * *